United States Patent
Cassin (10) Patent No.: US 7,780,955 B2
(45) Date of Patent: Aug. 24, 2010

(54) COSMETIC COMPOSITION WITH A LIGHTENING EFFECT

(75) Inventor: Guillaume Cassin, Villebon sur Yvette (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 11/272,318

(22) Filed: Nov. 14, 2005

(65) Prior Publication Data

US 2006/0134033 A1 Jun. 22, 2006

Related U.S. Application Data

(60) Provisional application No. 60/645,075, filed on Jan. 21, 2005.

(30) Foreign Application Priority Data

Nov. 12, 2004 (FR) .................... 04 52611

(51) Int. Cl.
- A61Q 1/02 (2006.01)
- A61Q 19/04 (2006.01)
- A61Q 1/00 (2006.01)
- A61Q 1/12 (2006.01)
- A61K 8/00 (2006.01)
- A61K 8/18 (2006.01)

(52) U.S. Cl. .......................... 424/63; 424/69
(58) Field of Classification Search ............... 424/69, 424/63
See application file for complete search history.

(56) References Cited

U.S. PATENT DOCUMENTS

| 5,223,559 A | 6/1993 | Arraudeau et al. |
| 5,412,004 A | 5/1995 | Tachibana et al. |
| 5,538,793 A | 7/1996 | Inokuchi et al. |
| 5,690,916 A | 11/1997 | Kimura et al. |
| 5,811,487 A | 9/1998 | Schulz, Jr. et al. |
| 6,117,435 A | 9/2000 | Painter et al. |
| 6,428,773 B1 * | 8/2002 | Oko et al. ............... 424/63 |
| 2003/0017124 A1 * | 1/2003 | Agostini et al. ............... 424/63 |
| 2003/0064039 A1 * | 4/2003 | Kolodziej et al. ............... 424/63 |
| 2005/0169950 A1 | 8/2005 | Delacour et al. |

FOREIGN PATENT DOCUMENTS

| EP | 0 701 810 A1 | 3/1996 |
| JP | A-10-503515 | 3/1998 |
| JP | A 2000-191789 | 7/2000 |
| JP | A-2002-518420 | 6/2002 |
| JP | A-2002-538091 | 11/2002 |
| JP | A 2003-128788 | 5/2003 |
| JP | 2003165921 A * | 6/2003 |
| JP | A-2004-83422 | 3/2004 |
| JP | A-2004-526694 | 9/2004 |
| WO | WO 96/03962 A1 | 2/1996 |
| WO | WO 99/66883 | 12/1999 |
| WO | WO 00/51551 | 9/2000 |
| WO | WO 00/71093 A1 | 11/2000 |
| WO | WO 01/51017 A2 | 7/2001 |
| WO | WO 02/053126 A1 | 7/2002 |
| WO | WO 02/056846 A1 | 7/2002 |
| WO | WO 2004/045524 A2 | 6/2004 |

OTHER PUBLICATIONS

Wiley, "Encyclopedia of Chemical Technology, Kirk-Othmer", vol. 22, pp. 333-432, $3^{rd}$ Edition, 1979. Definition for the properties and functions (emulsifying) of surfactants, for example pp. 347-377.

* cited by examiner

Primary Examiner—Shengjun Wang
Assistant Examiner—Kendra D Carter
(74) Attorney, Agent, or Firm—Oliff & Berridge, PLC (57) ABSTRACT

A cosmetic composition for making up and/or caring for the skin and/or the lips, has, in a physiologically acceptable medium, at least interference particles with a volume-average size of less than 40 μm and at least one filler such that the composition also has a lightness L* of greater than 60 and a saturation C* of less than 10.

18 Claims, 2 Drawing Sheets

COSMETIC COMPOSITION WITH A LIGHTENING EFFECT

CROSS-REFERENCE TO RELATED APPLICATIONS

This non-provisional application claims the benefit of French Application No. 04 52611 filed on Nov. 12, 2004 and U.S. Provisional. Application No. 60/645,075 filed on Jan. 21, 2005, the entire disclosures of which are incorporated herein by reference.

BACKGROUND

The present invention relates to cosmetic compositions for making up and/or caring for the skin and the lips, and which are for example useful for giving the skin and the lips a lightening, unifying or even covering effect with regard to skin imperfections.

It is common for people with dyschromia, for instance pigmentation marks, blotchy skin or shadows on the skin and for example on the face, to wish to efface these skin defects. Similarly, people with colored skin may wish to lighten the natural shade of their skin.

As more particularly regards the lightening aspect of the skin, it is already known practice to use products containing bleaching active agents, for instance hydroquinone. However, these products have the effect of being relatively aggressive and moreover of requiring a prolonged treatment before obtaining a result. They therefore do not afford an immediate lightening effect as soon as they are applied to the skin.

Other alternative compositions have already been proposed to obtain an immediate lightening and/or covering effect.

A first alternative exploits fluorescent compounds such as optical brighteners. However, these compounds only afford an immediate lightening effect under optimum lighting conditions, which are generally better than those afforded by natural light or ordinary lighting.

A second alternative is directed towards using "interference" pigments, i.e. pigments capable of affording a colored glint that differs according to the angle of observation. Unfortunately, these compositions generally have the drawback of simultaneously giving a glossy appearance and are therefore not in accordance with the natural flesh tone of the skin. Moreover, these interference pigments are generally used under conditions such that the corresponding cosmetic composition gives an excessively imperfect colored and/or covering effect that therefore masks the skin's natural appearance. Such compositions are especially described in documents WO 01/51017 and U.S. Pat. No. 5,690,916.

Another alternative described in document WO 04/045524 is itself directed towards combining in the same composition "transparent" pigments with non-interference particles. However, this type of composition does not prove to be entirely satisfactory in terms of covering dyschromia.

Consequently, there is still a need for a cosmetic composition that can give a lightening and unifying makeup while at the same time preserving the skin's natural flesh tone in terms of color and/or sheen.

SUMMARY

The inventors have specifically demonstrated, unexpectedly, that it is possible to formulate such a cosmetic composition, i.e. a composition having an immediate and prolonged lightening and/or homogenizing effect on the complexion, subject to selecting particular interference particles.

According to one exemplary embodiment, the present invention relates to a cosmetic composition for making up and/or caring for the skin and/or the lips, comprising, in a physiologically acceptable medium, at least interference particles with a volume-average size of less than 40 μm and at least one filler, the said composition also having a lightness $L^*$ of greater than 60 and a saturation $C^*$ of less than 5.

According to another exemplary embodiment, the present invention relates to a cosmetic composition for making up and/or caring for the skin and/or the lips, comprising, in a physiologically acceptable medium, at least interference particles with a volume-average size of less than 40 μm and at least one filler, said composition also having a lightness $L^*$ of greater than 75 and a saturation $C^*$ of less than 10.

According to another exemplary embodiment, the present invention relates to a cosmetic composition for making up and/or caring for the skin and/or the lips, comprising, in a physiologically acceptable medium, at least interference particles with a volume-average size of less than 40 μm and at least one filler chosen from porous silica microparticles, polytetrafluoroethylene powders, silicone resin powders, hemispherical hollow silicone particles, acrylic copolymer powders, wax powders, polyethylene powders, crosslinked elastomeric organopolysiloxane powders coated with silicone resin, talc/titanium dioxide/alumina/silica composite powders, polyamide powders, and mixtures thereof, said composition also having a lightness $L^*$ of greater than 60 and a saturation $C^*$ of less than 10.

According to another exemplary embodiment, the present invention relates to a cosmetic composition for making up and/or caring for the skin and/or the lips, comprising, in a physiologically acceptable medium, at least interference particles with a volume-average size of less than 40 μm and at least one filler with matting power, said filler being such that it gives the said composition a matting power of less than 1, for example less than or equal to 0.75, said cosmetic composition also having a lightness $L^*$ of greater than 60 and a saturation $C^*$ of less than 10.

According to yet another exemplary embodiment, the present invention relates to a cosmetic composition for making up and/or caring for the skin and/or the lips, comprising, in a physiologically acceptable medium, at least interference particles with a volume-average size of less than 40 μm and at least one filler, said filler being in an amount such that the filler/interference particle weight ratio ranges from 0.3 to 2.5 and in particular from 0.5 to 1.2, said cosmetic composition also having a lightness $L^*$ of greater than 60 and a saturation $C^*$ of less than 10.

According to yet another exemplary embodiment, the present invention relates to a cosmetic composition for making up and/or caring for the skin and/or the lips, comprising, in a physiologically acceptable medium, at least interference particles with a volume-average size of less than 40 μm and at least one filler chosen for example according to its nature, its particle size and/or its amount, to give the said composition a variation in reflectance, measured for a range of angles of observation ranging from 0 to 80° and at a wavelength corresponding to the region of the spectrum in which the reflectance of the associated interference particles is the greatest, such that, firstly, the maximum reflectance measured at the top of the reflection peak is less than 150%, for example less than 100% and for example less than 75%, and, secondly, the minimum reflectance measured at the base of the reflection peak is greater than 5%, said composition also having a lightness L* of greater than 60 combined with a saturation C* of less than 10.

According to yet another exemplary embodiment, the present invention is directed towards the cosmetic use of a composition as defined above, for obtaining a lightening and/or homogenizing effect on the skin and/or the lips. In embodiments, methods for obtaining a lightening and/or homogenizing effect on skin and/or lips include applying a composition according to the present invention to the skin and/or lips in an amount sufficient to provide the lightening and/or homogenizing effect.

According to yet another exemplary embodiment, the present invention is directed towards the cosmetic use of a composition as defined above for covering skin dyschromia. In embodiments, methods for covering skin dyschromia include applying a composition according to the present invention to cover an area of skin having dyschromia.

According to yet another exemplary embodiment, the present invention is directed towards a process for making up the skin and/or the lips, comprising at least the application to the skin and/or the lips of a composition as defined above.

The inventors have thus demonstrated that a selection of specific interference particles and a combination thereof with a filler, which is, where appropriate, also a particular filler, advantageously makes it possible to obtain a makeup effect that has improved transparency and an improved lightening effect when compared with conventional compositions.

BRIEF DESCRIPTION OF THE DRAWINGS

The invention can be better understood on reading the following detailed description of non-limiting embodiments thereof, and on observing the accompanying drawings, in which.

DETAILED DESCRIPTION OF EMBODIMENTS

For the purposes of the present invention, the term "transparency" is intended to characterize the fact that the makeup effect and/or care effect afforded by the said composition on the skin hardly affects, or does not at all affect, the skin's natural flesh tone. Thus, the compositions according to the invention have the advantage of not giving a covering or shiny appearance, and thus of optimally preserving the natural flesh tone of the skin onto which they are applied. The compositions according to the invention differ in this respect from standard foundation compositions, which, in general, affect the skin's natural flesh tone, by significantly darkening or modifying its natural coloration or, conversely, by excessively lightening it, or alternatively by giving it an excessively shiny appearance.

Lightness L* and Saturation C*

The natural effect afforded by the compositions according to the invention may for example be characterized by the lightness L* and saturation C* colorimetric values measured in the CIE 1976 colorimetric space.

The colorimetric measurements L* and C* may be performed using a Minolta CR400® colorimetric Chromameter. To do this, the test composition is introduced into a 15 ml jar (aperture diameter: 1.9 cm; depth: 1.8 cm). The surface of the composition introduced is smoothed out by flattening with a glass slide. The colorimeter cell is then placed in contact with this surface and the colorimetric parameters are determined.

For information, the white reference supplied with the Chromameter CR400® colorimeter is characterized by the following lightness L* and saturation C* values:

L*=96.94+/−0.01, C*=2.83+/−0.01

According to one exemplary embodiment, the compositions according to the invention may be characterized by a lightness L* of greater than 60 combined with a saturation C* of less than 5.

According to another exemplary embodiment, the compositions according to the invention may be characterized by a lightness L* of greater than 75 combined with a saturation C* of less than 10.

In one exemplary embodiment, the compositions according to the invention may be characterized by a lightness L* of greater than 60, for example greater than 80 and for example greater than 86.

In one exemplary embodiment, the compositions according to the invention may be characterized by a saturation C* of less than 5, for example less than 3 and for example less than 2.

For example, the compositions in accordance with these requirements may be white in the bulk. They may also contain less than 5% and for example less than 2% by weight of metal oxide(s).

Interference Particles

For the purposes of the present invention, the term "interference particles" denotes any particle generally having a multilayer structure such that it allows the creation of a color effect by interference of the light rays that diffract and diffuse differently according to the nature of the layers. Thus, these particles may have colors that vary according to the angle of observation and the incidence of the light.

For the purposes of the present invention, a multilayer structure is intended to denote either a structure formed from a substrate covered with a single layer or a structure formed from a substrate covered with at least two or even more consecutive layers.

The multilayer structure may thus comprise one or even at least two layers, each layer, independently or otherwise of the other layer(s), being made of at least one material chosen from the group consisting of the following materials: $MgF_2$, $CeF_3$, $ZnS$, $ZnSe$, $Si$, $SiO_2$, $Ge$, $Te$, $Fe_2O_3$, $Pt$, $Va$, $Al_2O_3$, $MgO$, $Y_2O_3$, $S_2O_3$, $SiO$, $HfO_2$, $ZrO_2$, $CeO_2$, $Nb_2O_5$, $Ta_2O_5$, $TiO_2$, $Ag$, $Al$, $Au$, $Cu$, $Rb$, $Ti$, $Ta$, $W$, $Zn$, $MoS_2$, cryolite, alloys and polymers, and combinations thereof.

For example, the multilayer structure may be of mineral nature.

In one exemplary embodiment, the interference particles under consideration according to the invention may be interference pigments, or alternatively natural or synthetic, monolayer or multilayer nacres, for example formed from a natural substrate based, inter alia, on mica, which may be covered with one or more layers of metal oxide.

The interference particles according to the invention may be characterized by a volume-average size generally of less than 40 μm, for example ranging from 0.5 to 40 μm, for example less than 30 μm, for example less than 20 μm, for example less than 15 μm, and for example ranging from 1 to 15 μm, measured with a laser granulometer, for instance the Mastersizer 2000® machine from Malvern and/or the BI90+® machine from Brookhaven Instrument Corporation.

Nacres of mica/tin oxide/titanium oxide type, for instance those sold under the names Timiron Silk Blue®, Timiron Silk Red®, Timiron Silk Green®, Timiron Silk Gold® and Timiron Super Silk® sold by the company Merck, and mica/iron oxide/titanium oxide nacres, for instance Flamenco Satin Blue®, Flamenco Satin Red® and Flamenco Satin Violet® sold by the company Engelhard, and mixtures thereof, are for example suitable for the invention.

It is understood that the choice of these interference particles is made so as to be moreover compatible with the requirements in terms of lightness and saturation required for the compositions according to the invention. For example, these interference particles are present in an amount sufficient to obtain a homogeneous effect in terms of coloration while at the same time preserving the natural flesh tone of the skin and/or the lips.

In one exemplary embodiment, these particles may be present in an amount of less than 15%, for example ranging from 0.5% to 15%, for example from 1% to 10%, for example less than 7%, for example less than 5% and for example ranging from 2% to 5% by weight relative to the total weight of the composition.

Fillers

For the purposes of the present invention, the term "filler" denotes any material consisting of spherical or non-spherical, porous or non-porous particles that are insoluble in the compositions according to the invention.

As stated previously, the presence of a filler in combination with interference particles is advantageous in so far as it contributes towards affording improved spatial homogenization of the glint afforded by these particles.

In general, the glint of an interference particle is observable only for certain angles of observation, also known as angles of angular reflection. Consequently, the angular distribution of the colored glint is narrow and the color correction provided by the use of these particles is therefore non-homogeneous in its spatial distribution.

The inventors have found, unexpectedly, that by combining fillers, and for example matting fillers, with small interference particles, it is possible to increase the angular distribution of the colored glint afforded by these interference particles.

This effect may for example be evaluated according to the following technique.

Figure 1:
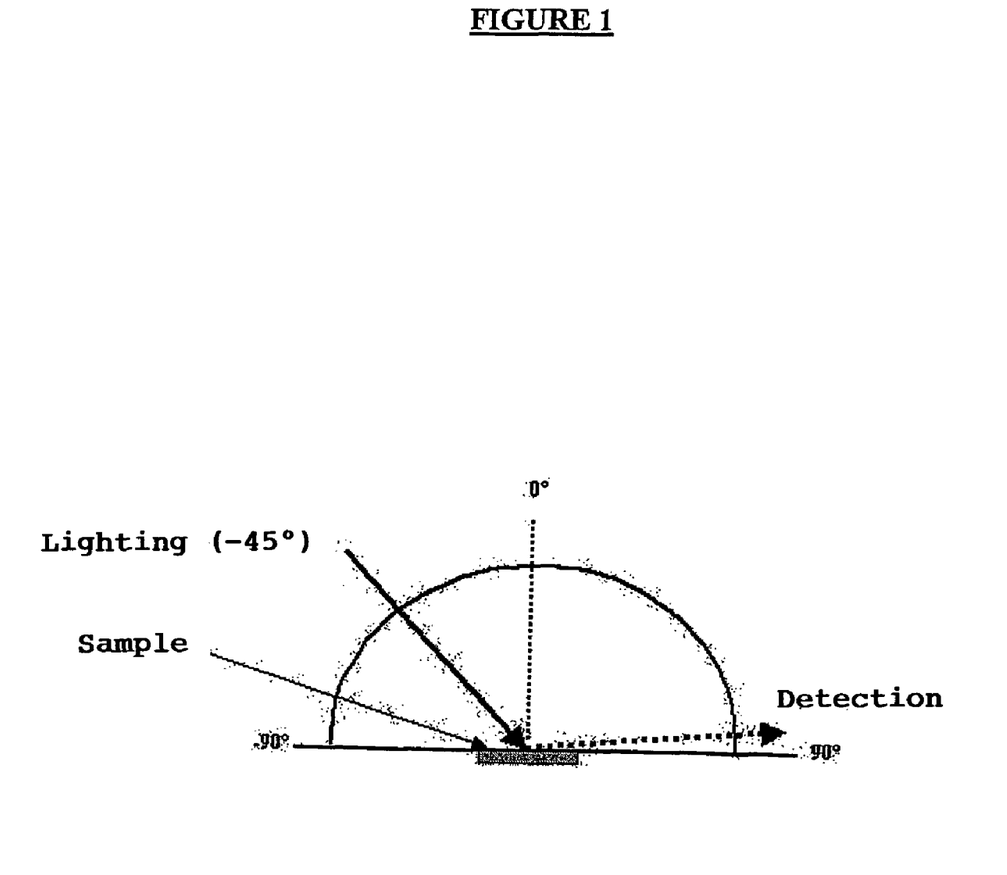
FIG. 1 is a schematic depiction showing exemplary geometry according to which angular distribution of colored glint afforded by interference particles may be measured.

In the case of a fluid composition, the test composition is spread in the form of a film whose thickness measured at the time of deposition, i.e. before air-drying, is 30 µm, onto an Erichsen type 24/5 contrast card using an automatic applicator from Braive Instruments. The spread composition is then placed in a thermostatically regulated and ventilated oven for 24 hours at 37° C. The measurements are taken on the black background of the contrast card using a GON 360® spectrogonioreflectometer sold by the company Instrument System, according to the geometry shown in FIG. 1.

The change in reflectance is assessed as a function of the angle of observation at the wavelength corresponding to the region of the spectrum in which the reflectance of the type of interference particles or of the mixture of several types of interference particles under consideration according to the invention is the greatest.

In the case of non-fluid cosmetic compositions, the application of the said composition to the contrast card may be performed according to the following instructions:

For compacted powders, they are decompacted so as to convert them into loose powders. The powder is deposited homogeneously onto a flat surface and an adhesive transparent plastic film is then applied onto the powder with a pressure of 100 g/cm$^2$, so that the powder sticks to the adhesive and an adhesive surface saturated with powder is obtained. The powder-bearing adhesive face is then placed against a transparent glass plate and the assembly is placed on the contrast card. The measurements are performed as previously.

For a stick, it may be melted so as to be placed in the form of a layer 20 µm thick onto a transparent film. It is left to dry for 10 minutes at 37° C. in an oven and the film is then applied to the contrast card, in the same manner as has been described above.

For the case of a spray, a thickness of 20 µm of composition is applied and left to dry for 10 minutes at 37° C. in an oven.

In the context of a composition according to the invention, homogenization of the color is thus observed under all the angles of observation when the interference particles are combined with a filler.

For example, the filler under consideration according to the invention may be chosen in terms of nature, particle size and/or amount so as to give the said composition a variation in reflectance defined such that, firstly, the maximum reflectance measured at the top of the reflection peak is less than 150%, for example less than 100% and for example less than 75%, and, secondly, the minimum reflectance measured at the bottom of the reflection peak is greater than 5%. This variation in reflectance is measured for a range of angles of observation ranging from 0 to 80° and at the wavelength corresponding to the region of the spectrum in which the reflectance of the combined interference particles is the greatest.

According to one exemplary embodiment, the materials used as filler may have a particle size, expressed on a volume basis, comparable to that of the interference particles.

Thus, the fillers have for example a size by volume of less than 40 µm, for example ranging from 0.5 to 40 µm, for example less than 30 µm, for example less than 15 µm and for example ranging from 1 to 15 µm.

In one exemplary embodiment, the composition according to the invention may contain various fillers, of mineral or organic origin. These fillers may be of any form, for example platelet-shaped, spherical or oblong, irrespective of their crystallographic form (for example lamellar, cubic, hexagonal, orthorhombic, etc.).

According to one exemplary embodiment, these fillers may be spherical.

According to another exemplary embodiment, these fillers may also be porous. This porosity may for example be reflected by a specific surface area of the particles of greater than 10 m$^2$/g, for example ranging from 20 m$^2$/g to 5000 m$^2$/g, for example greater than 50 m$^2$/g, for example ranging from 50 m$^2$/g to 3000 m$^2$/g, and for example ranging from 100 m$^2$/g to 1000 m$^2$/g.

According to one exemplary embodiment of the invention, the fillers under consideration may be "matting" fillers, i.e. fillers with a refractive index of less than or equal to 2.2, for example less than or equal to 2, for example less than or equal to 1.8 and for example ranging from 1.3 to 1.6.

The refractive index of the particles may be evaluated via the "contrast erasure" method. By selecting two fully miscible solvents with relatively different refractive indices (ethanol: 1.36 and phenylethyl alcohol: 1.529), it is possible to prepare mixtures that have intermediate refractive indices. The particles in question are suspended in these various solvent mixtures and the transparency of these solutions is then evaluated using a Hach 2100P® turbidimeter sold by the company Hach. The refractive index of the particle is equal to that of the solvent mixture for which the least turbid solution is obtained, i.e. the least cloudy solution, which corresponds to the minimum difference in refractive index between the particles and the solvent mixture.

In the exemplary embodiment case in which the fillers under consideration according to the invention are matting fillers, the matting power of the compositions containing them may be characterized by means of the following protocol.

The test composition is spread at a rate of 2 mg/cm$^2$ onto a contrast card (Prufkarte type 24/5-250 cm$^2$ sold by the company Erichsen) using a mechanical film spreader. The composition is then dried overnight at a temperature of 37° C. before measuring its reflection using a gonioreflectometer sold by the company Micromodule. The result obtained is the ratio R between the specular reflection and the diffuse reflection. The value of R is proportionately smaller the greater the matting effect afforded by the filler.

In the context of the present invention, the matting filler under consideration may for example be chosen such that it gives the said composition a matting power of less than 1, for example ranging from 0.1 to 0.8, for example less than 0.75 and for example ranging from 0.15 to 0.75.

In one exemplary embodiment, the matting fillers may have a size by volume of less than 40 μm, for example ranging from 0.5 to 40 μm and for example from 1 to 15 μm.

Fillers that may for example be suitable for the invention, for example as fillers with matting power, are those chosen from:

polytetrafluoroethylene powders, for instance the Cridust 9205F® PTFEs from Clariant, with a mean size of 8 μm;

silicone resin powders, for instance the Tospearl 145A® silicone resins from GE Silicone, with a mean size of 4.5 μm;

wax powders, for instance the Paraffin Wax Microease 114S® particles from Micropowders, with a mean size of 7 μm;

polyethylene powders, especially comprising at least one ethylene/acrylic acid copolymer and in particular consisting of ethylene/acrylic acid copolymers, for instance the Flobeads EA 209® particles from Sumitomo, with a mean size of 10 μm;

polyamide powders (Nylon®), for instance the Nylon 12 particles of the Orgasol® type from Atofina, with a mean size of 10 μm;

porous silica microparticles, for instance the Silica Beads SB150® and SB700® from Miyoshi, with a mean size of 5 μm, and the Sunspheres Series H® from Asahi Glass, for instance Sunsphere H33®, H51® and H53®, with respective sizes of 3, 5 and 5 μm;

hollow hemispherical silicone particles, for instance NLK 500®, NLK 506® and NLK 510® from Takemoto Oil and Fat;

acrylic copolymer powders, especially of polymethyl (meth)acrylate, for instance the PMMA Jurimer MBI® particles from Nihon Junyoki, with a mean size of 8 μm, the vinylidene/acrylonitrile/methylene methacrylate expanded microspheres sold under the name Expancel®; and more particularly the hollow PMMA spheres sold under the name Covabead LH85® by the company Wacker;

crosslinked elastomeric organopolysiloxane powders coated with silicone resin, especially with silsesquioxane resin, as described, for example, in U.S. Pat. No. 5,538,793. Such elastomer powders are sold under the names KSP-100®, KSP-101®, KSP-102®, KSP-103®, KSP-104® and KSP-105® by the company Shin-Etsu;

talc/titanium dioxide/alumina/silica composite powders, for instance those sold under the name Coverleaf AR-80® by the company Catalyst & Chemicals;

and mixtures thereof.

Among the abovementioned powders, the last five types of powder and mixtures thereof may for example be suitable in the invention.

As regards the hollow hemispherical silicone particles, they may be portions of bowl-shaped hollow spheres. These may be obtained as described in patent application JP-2003 128 788. Portions of horseshoe-shaped hollow spheres are also described in patent application JP-A-2000-191 789.

These particles may for example be methyl silanol/silicate crosspolymer particles, for instance the trade names NLK 500, NLK 506 and NLK 510.

As illustrations of other fillers that may be suitable for the invention, mention may be for example of talc, mica, kaolin, colloidal silica, poly-(3-alanine, polyethylene, lauroyllysine, starch, boron nitride, micronized polytetrafluoroethylene powders, precipitated calcium carbonate, magnesium carbonate, magnesium hydrogen carbonate, barium sulfate, hydroxyapatite, glass or ceramic microcapsules, and metal soaps derived from organic carboxylic acids containing from 8 to 22 carbon atoms and for example from 12 to 18 carbon atoms, for example zinc stearate, magnesium stearate, lithium stearate, zinc laurate or magnesium myristate, and mixtures thereof.

As mentioned previously, the filler under consideration according to the invention is present in an amount sufficient to afford improved spatial homogenization of the glint afforded by the combined interference particles.

For obvious reasons, this amount is liable to vary significantly depending on the nature and/or the particle size of the filler or of the mixture of filler(s).

For example, the filler may be present in a proportion of less than 15% by weight and for example ranging from 0.5% to 15% by weight, for example in a proportion of less than 10% and for example ranging from 1% to 10% by weight, for example in a proportion of less than 5% by weight and for example ranging from 2% to 5% by weight relative to the total weight of the composition.

According to one exemplary embodiment variant of the invention, the amount of filler is adjusted such that the filler/interference particle weight ratio ranges from 0.3 to 2.5 and for example is greater than or equal to 0.5 and for example greater than or equal to 0.8.

Physiologically Acceptable Medium

The interference particles and the fillers according to the invention may be conditioned in a physiologically acceptable medium constituting the support for the cosmetic composition.

The term "physiologically acceptable medium" denotes a non-toxic medium that can be applied to human skin and/or lips. The physiologically acceptable medium is generally suited to the nature of the skin onto which the composition is to be applied and also to the form in which the composition is intended to be conditioned, for example fluid or non-fluid at room temperature and at atmospheric pressure.

Thus, the compositions according to the invention may be formulated in a fluid or solid form of loose, compact or cast powder type.

According to one exemplary embodiment of the invention, they may comprise at least one aqueous phase, and for example water combined, where appropriate, with a fatty phase.

Aqueous Phase

The composition according to the invention may comprise at least one aqueous medium, constituting an aqueous phase, which can form the continuous phase of the composition under consideration.

This aqueous phase may consist totally or partially and for example consists essentially of water.

It may also comprise a mixture of water and of water-miscible organic solvent (miscible in water to greater than 50% by weight at 25° C.), for instance lower monoalcohols containing from 1 to 5 carbon atoms, such as ethanol, isopropanol, glycols containing from 2 to 8 carbon atoms, such as propylene glycol, ethylene glycol, 1,3-butylene glycol, dipropylene glycol, $C_3$-$C_4$ ketones and $C_2$-$C_4$ aldehydes.

The aqueous phase (water and optionally the water-miscible organic solvent) may be present in a content ranging from 1% to 95% by weight, for example ranging from 3% to 80% by weight, and for example ranging from 5% to 60% by weight, relative to the total weight of the composition under consideration.

Such a medium may also comprise a volatile oil as defined below.

The composition according to the invention may also contain, for example, a continuous fatty phase, which may contain less than 5% of water and for example less than 1% of water relative to its total weight, and may for example be in anhydrous form.

Fatty Phase

The fatty phase may for example comprise at least one fatty substance that is liquid at room temperature (25° C.) and/or a fatty substance that is solid at room temperature, such as waxes, pasty fatty substances and gums, and mixtures thereof. The fatty phase may also contain lipophilic organic solvents.

The fatty phase of the composition according to the invention may for example comprise, as liquid fatty substance, at least one volatile or non-volatile oil or a mixture thereof.

For the purposes of the invention, the term "volatile oil" means any oil capable of evaporating on contact with the skin in less than one hour, at room temperature and atmospheric pressure. The volatile oils of the invention are volatile cosmetic oils, which are liquid at room temperature, having a non-zero vapour pressure, at room temperature and atmospheric pressure, ranging for example from 0.01 to 300 mmHg (1.33 Pa to 40 000 Pa) and for example greater than 0.3 mmHg (30 Pa).

The term "non-volatile oil" means an oil that remains on the skin at room temperature and atmospheric pressure for at least several hours and that for example has a vapour pressure of less than 0.01 mmHg (1.33 Pa).

These volatile or non-volatile oils may be hydrocarbon-based oils, silicone oils or mixtures thereof. The term "hydrocarbon-based oil" means an oil mainly containing hydrogen and carbon atoms and possibly oxygen, nitrogen, sulfur and phosphorus atoms.

The volatile hydrocarbon-based oils may be chosen from hydrocarbon-based oils containing from 8 to 16 carbon atoms, and for example branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane, and for example the oils sold under the trade names Isopar® and Permethyl®, branched $C_8$-$C_{16}$ esters such as isohexyl neopentanoate, and mixtures thereof. Other volatile hydrocarbon-based oils, for instance petroleum distillates, for example those sold under the name Shell Solt® by the company Shell, may also be used.

Volatile oils that may also be used include volatile silicones, for instance volatile linear or cyclic silicone oils, for example those with a viscosity 8 centistokes ($8 \times 10^{-6}$ m$^2$/s) and for example containing from 2 to 7 silicon atoms, these silicones optionally comprising alkyl or alkoxy groups containing from 1 to 10 carbon atoms. As volatile silicone oils that may be used in the invention, mention may be made for example of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The volatile oil may be present in a composition according to the invention in a content ranging from 0.1% to 98% by weight, for example from 1% to 65% by weight and for example from 2% to 50% by weight relative to the total weight of the composition.

The non-volatile oils may be chosen for example from non-volatile hydrocarbon-based fluoro and/or silicone oils.

Non-volatile hydrocarbon-based oils that may for example be mentioned include:

hydrocarbon-based oils of animal origin, hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are for example wheatgerm oil, sunflower oil, grapeseed oil, sesame seed oil, maize oil, apricot oil, castor oil, shea oil, avocado oil, olive oil, soybean oil, sweet almond oil, palm oil, cottonseed oil, hazelnut oil, macadamia oil, jojoba oil, alfalfa oil, poppyseed oil, pumpkin oil, sesame seed oil, marrow oil, rapeseed oil, blackcurrant oil, evening primrose oil, millet oil, barley oil, quinoa oil, rye oil, safflower oil, candlenut oil, passionflower oil or musk rose oil; shea butter; or caprylic/capric acid triglycerides, for instance those sold by the company Stéarineries Dubois or those sold under the names Miglyol 810, 812 and 818® by the company Dynamit Nobel, synthetic ethers containing from 10 to 40 carbon atoms;

linear or branched hydrocarbons of mineral or synthetic origin, such as petroleum jelly, polydecenes, hydrogenated polyisobutene such as parleam, and squalane, and mixtures thereof, synthetic esters, for instance oils of formula $R_1COOR_2$ in which $R_1$ represents a linear or branched fatty acid residue containing from 1 to 40 carbon atoms and $R_2$ represents a hydrocarbon-based chain, which is for example branched, containing from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, alcohol or polyalcohol heptanoates, octanoates, decanoates or ricinoleates, for instance propylene glycol dioctanoate; hydroxylated esters, for instance isostearyl lactate or diisostearyl malate; polyol esters and pentaerythritol esters, fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol, higher fatty acids such as oleic acid, linoleic acid or linolenic acid, and mixtures thereof.

The non-volatile silicone oils that may be used in the composition according to the invention may be non-volatile polydimethylsiloxanes (PDMS), polydimethylsiloxanes comprising alkyl or alkoxy groups, which are pendant and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates.

The non-volatile oils may be present in a composition according to the invention in a content ranging from 0.01% to 90% by weight, for example from 0.1% to 85% by weight and for example from 1% to 70% by weight relative to the total weight of the composition.

In one exemplary embodiment, the liquid fatty substance may be present in a proportion of from 0.01% to 90% by weight and for example from 0.1% to 85% by weight relative to the weight of the fatty phase.

As regards the fatty substance that is solid at room temperature and atmospheric pressure, it may be chosen from waxes, pasty fatty substances and gums, and mixtures thereof. This solid fatty substance may be present in a proportion of from 0.01% to 50%, for example from 0.1% to 40% and for example from 0.2% to 30% by weight relative to the total weight of the fatty phase.

Surfactants

The composition according to the invention may also contain emulsifying and co-emulsifying surfactants, present for example in a proportion ranging from 0.1% to 30% by weight and for example from 5% to 15% by weight relative to the total weight of the composition.

These surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, for example pp. 347-377 of this reference, for the anionic and nonionic surfactants.

As surfactants that may be used in the invention, which are suitable for obtaining a W/O emulsion, mention may be made for example of dimethicone copolyols such as the mixture of cyclomethicone and of dimethicone copolyol, sold under the name "DC 5225 C" by the company Dow Corning, and dimethicone copolyols, such as the laurylmethicone copolyol sold under the name Dow Corning 5200 Formulation Aid® by the company Dow Corning, the cetyldimethicone copolyol sold under the name Abil EM 90® by the company Goldschmidt, or the mixture of cetyldimethicone copolyol, polyglyceryl-4 isostearate and hexyl laurate, sold under the name Abil WE 09® by the company Goldschmidt.

One or more coemulsifiers may also be added thereto, which may be for example chosen from the group comprising alkylated esters of polyol. Alkylated esters of polyol that may for example be mentioned include glycerol and/or sorbitan esters, for example polyglyceryl isostearate, such as the product sold under the name Isolan GI 34® by the company Goldschmidt, sorbitan isostearate, such as the product sold under the name Arlacel 987® by the company ICI, sorbitan glyceryl isostearate, such as the product sold under the name Arlacel 986® by the company ICI, and mixtures thereof.

Polyisobutylene surfactants containing esterified succinic end groups, such as those sold under the names Lubrizol 5603® and Chemcinnate 2000® by the companies Lubrizol and Chemron, are for example suitable as emulsifier suitable for obtaining a W/O emulsion.

Surfactants for W/O emulsions that may also be used include a crosslinked elastomeric solid organopolysiloxane comprising at least one oxyalkylene group, such as those obtained according to the procedure of Examples 3, 4 and 8 of document U.S. Pat. No. 5,412,004 and of the examples of document U.S. Pat. No. 5,811,487, for example the product of Example 3 (synthesis example) of U.S. Pat. No. 5,412,004, and such as the product sold under the reference KSG 21® by the company Shin-Etsu.

As surfactants that may be used in the invention, which are suitable for obtaining an O/W emulsion, examples that may be mentioned include nonionic surfactants, and for example esters of polyols and of fatty acids with a saturated or unsaturated chain containing, for example, from 8 to 24 carbon atoms and for example from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof the polyethylene glycol esters of $C_8$-$C_{24}$ fatty acids, and the oxyalkylenated derivatives thereof the sorbitol esters of $C_8$-$C_{24}$ fatty acids, and the oxyalkylenated derivatives thereof the sugar (sucrose, glucose or alkylglucose) esters of $C_8$-$C_{24}$ fatty acids, and the oxyalkylenated derivatives thereof the ethers of fatty alcohols; the sugar ethers of $C_8$-$C_{24}$ fatty alcohols; the oxyethylenated fatty acid ethers of glucose or of alkylglucose; and mixtures thereof.

Glyceryl esters of fatty acids that may for example be mentioned include glyceryl stearate (glyceryl mono-, di- and/or tristearate) (CTFA name: glyceryl stearate) or glyceryl ricinoleate and mixtures thereof.

Polyethylene glycol esters of fatty acids that may for example be mentioned include polyethylene glycol stearate (polyethylene glycol mono-, di- and/or tristearate) and for example polyethylene glycol 500E monostearate (CTFA name: PEG-50 stearate), polyethylene glycol 1000E monostearate (CTFA name: PEG-100 stearate) and mixtures thereof.

It is also possible to use mixtures of these surfactants, for instance the product containing glyceryl stearate and PEG-100 stearate, sold under the name Arlacel 165® by the company Uniqema, and the product containing glyceryl stearate (glyceryl mono-distearate) and potassium stearate, sold under the name Tegin® by the company Goldschmidt (CTFA name: glyceryl stearate SE).

Fatty acid esters of glucose or of alkylglucose that may be mentioned for example include glucose palmitate, alkylglucose sesquistearates, for instance methylglucose sesquistearate, alkylglucose palmitates, for instance methylglucose palmitate or ethylglucose palmitate, fatty esters of methylglucoside and for example the diester of methylglucoside and of oleic acid (CTFA name: Methyl glucose dioleate); the mixed ester of methylglucoside and of the oleic acid/hydroxystearic acid mixture (CTFA name: Methyl glucose dioleate/hydroxystearate); the ester of methylglucoside and of isostearic acid (CTFA name: Methyl glucose isostearate); the ester of methylglucoside and of lauric acid (CTFA name: Methyl glucose laurate); the mixture of the monoester and diester of methylglucoside and of isostearic acid (CTFA name: Methyl glucose sesquiisostearate); the mixture of the monoester and diester of methylglucoside and of stearic acid (CTFA name: Methyl glucose sesquistearate) and for example the product sold under the name Glucate SS® by the company Amerchol, and mixtures thereof.

Examples of oxyethylenated ethers of a fatty acid and of glucose or of alkylglucose that may be mentioned include the oxyethylenated ethers of a fatty acid and of methylglucose, and for example the polyethylene glycol ether of the diester of methyl-glucose and of stearic acid containing about 20 mol of ethylene oxide (CTFA name: PEG-20 methyl glucose distearate), such as the product sold under the name Glucam E-20 Distearate® by the company Amerchol; the polyethylene glycol ether of the mixture of monoester and diester of methylglucose and of stearic acid containing about 20 mol of ethylene oxide (CTFA name: PEG-20 methyl glucose sesquistearate) and for example the product sold under the name Glucamate SSE-20® by the company Amerchol, and the product sold under the name Grillocose PSE-20® by the company Goldschmidt, and mixtures thereof.

Examples of sucrose esters that may be mentioned include sucrose palmitostearate, sucrose stearate and sucrose monolaurate.

Examples of ethers of fatty alcohols that may be mentioned include polyethylene glycol ethers of fatty alcohols containing from 8 to 30 carbon atoms and for example from 10 to 22 carbon atoms, such as polyethylene glycol ethers of cetyl alcohol, stearyl alcohol or cetearyl alcohol (mixture of cetyl and stearyl alcohol). Examples that may be mentioned include ethers comprising from 1 to 200 and preferably from 2 to 100 oxyethylene groups, such as those of CTFA name Ceteareth-20 and Ceteareth-30, and mixtures thereof.

Sugar ethers that may for example be mentioned are alkylpolyglucosides, for example decylglucoside, for instance the product sold under the name Mydol 10® by the company Kao Chemicals, the product sold under the name Plantaren 2000® by the company Henkel, and the product sold under the name Oramix NS 10® by the company SEPPIC; caprylyl/capryl glucoside, for instance the product sold under the name Oramix CG 110 by the company SEPPIC or under the name Lutensol GD 70® by the company BASF; laurylglucoside, for instance the products sold under the names Plantaren 1200 N® and Plantacare 1200® by the company Henkel; cocoglucoside, for instance the product sold under the name Plantacare 818/UP® by the company Henkel; cetostearyl glucoside optionally as a mixture with cetostearyl alcohol, sold, for example, under the name Montanov 68® by the company SEPPIC, under the name Tego-Care CG90® by the company Goldschmidt and under the name Emulgade KE3302® by the company Henkel; arachidyl glucoside, for example in the form of the mixture of arachidyl alcohol and behenyl alcohol and arachidyl glucoside, sold under the name Montanov 202® by the company SEPPIC; cocoylethylglucoside, for example in the form of a mixture (35/65) with cetyl and stearyl alcohol, sold under the name Montanov 82® by the company SEPPIC, and mixtures thereof.

The composition according to the invention may also contain in one exemplary embodiment an amount of amphiphilic polymers as emulsifier or coemulsifier.

The term "amphiphilic polymer" means any polymer comprising both a hydrophilic portion and a hydrophobic portion and having the property of forming a film that separates two liquids of different polarity and thus making it possible to stabilize liquid-liquid dispersions of direct, inverse or multiple type. The amphiphilic polymers that are for example suitable reduce the water/oil interface tension to 10 mN/m, irrespective of the oil. These polymers are ionic (anionic or cationic) or amphoteric. They may be water-soluble or water-dispersible. The term water-soluble means that they can be dispersed in water in the form of a molecular solution. The term water-dispersible means that they can be dispersed in water in particulate form.

The amphiphilic polymers that may be suitable in the invention generally have a number-average molecular weight ranging from 1000 to 20 000 000 g/mol, for example ranging from 20 000 to 8 000 000 and for example from 100 000 to 700 000 g/mol. The amounts of amphiphilic polymers used according to the invention may be chosen from 0.01% to 20%, for example from 0.1% to 10% and for example from 0.2% to 5% by weight.

Acrylate/C10-C30-alkylacrylate copolymers such as the products sold under the names Pemulen TR1®, Pemulen TR2® and Carbobol 1382® by the company Goodrich, or mixtures thereof, may be used for example. The acrylate/steareth-20 itaconate copolymers and acrylate/ceteth-20 itaconate copolymers sold under the names Structure 2001® and Structure 3001® by the company National Starch may also be used. Among the crosslinked or non-crosslinked amphiphilic AMPS polymers that are for example suitable are the products sold under the names Aristoflex LNC®, Aristoflex SNC® and Aristoflex HMS® by the company Clariant.

As terpolymers that may be used, mention may be made of the methacrylic acid/methyl acrylate/behenyl dimethyl m-isopropenylbenzylisocyanate terpolymer ethoxylated with 40 OE, i.e. comprising 40 oxyethylene groups, sold by the company Amerchol under the name Viscophobe DB 1000 NP3-NP4®.

Mention may also be made of crosslinked terpolymers of methacrylic acid, of ethyl acrylate and of polyethylene glycol (100E) stearyl ether (Steareth 10), for example those sold by the company Allied Colloids under the name Salcare SC 80®.

The anionic polymers that may be used according to the invention are, for example, isophthalic acid or sulfoisophthalic polymers, and for example the phthalate/sulfoisophthalate/glycol copolymers (for example diethylene glycol/phthalate/isophthalate/1,4-cyclohexanedimethanol) sold under the names "Eastman AQ polymer" (AQ35S, AQ38S, AQ55S, AQ48 Ultra) by the company Eastman Chemical.

Film-Forming Polymer

The composition according to the invention may also comprise at least one film-forming polymer.

In the present patent application, the term "film-forming polymer" means a polymer capable of forming, by itself or in the presence of an auxiliary film-forming agent, a continuous film that adheres to the skin and/or the lips.

A film-forming polymer capable of forming a hydrophobic film, i.e. a polymer whose film has a solubility in water at 25° C. of less than 1% by weight, may for example be used.

The compositions according to the invention may also contain standard adjuvants such as dyes, pigments, optical brighteners, fragrances, preserving agents, physical and chemical sunscreens, sequestrants and pH regulators (acids or bases), and mixtures thereof. Needless to say, the choice of adjuvants is made so as not to harm the effects desired by means of the application of the composition according to the invention to the skin and/or the lips.

In a known manner, the cosmetic composition of the invention may also contain active agents that are common in cosmetics. Mention may be made for example of any active agent known for its activity on ageing of the skin, for instance keratolytic agents and prodesquamating agents, for example α-hydroxy acids, β-hydroxy acids, α-keto acids, β-keto acids, retinoids and esters thereof, retinal and retinoic acid and derivatives thereof. Mention may also be made of vitamins, for instance vitamins B3, C or PP, B5, E and K1, and derivatives of these vitamins and for example esters thereof; free-radical scavengers, sunscreens; moisturizers, for instance polyols; ceramides; DHEA and derivatives thereof; coenzyme Q10; bleaching agents and depigmenting agents, for instance kojic acid, para-aminophenol derivatives and arbutin and derivatives thereof, and mixtures thereof.

The composition according to the invention may be in the form of a formulation for example for application to the face or the neck, a concealer product, a foundation corrector, a facial makeup cream or base, or a body or lip makeup composition.

In one exemplary embodiment, it is a care and/or makeup product for the skin and for example for the face.

The composition according to the invention may be in a solid form, for example a pulverulent, compacted or cast form, or in stick form or in the form of a fluid, for example a pasty or liquid fluid.

In one exemplary embodiment, it is in a fluid form of the type such as a soft paste, an ointment, of a solid or fluid pomade, for instance a cream. For example, it may be a serum (thickened aqueous solution), an aqueous gel or an oil-in-water or water-in-oil emulsion, but also an oil-water-oil, glycol-oil-water or water-oil-water multiple emulsion.

The composition may be manufactured via the known processes generally used in cosmetics.

The examples given below are presented as non-limiting illustrations of the field of the invention.

EXAMPLES

All of the cosmetic compositions below are prepared according to the following protocol:

Phase B is heated to about 75° C. and polyammonium acryldimethyltauramide is incorporated therein. The mixture is stirred until a homogeneous gel is obtained.

Phase A is heated to 75° C.

The emulsion is prepared by incorporating Phase A into Phase B.

At 40-45° C., Phase C is incorporated and stirring is continued until cooling is complete.

Example 1

Control Cosmetic Composition

| | | |
|---|---|---|
| A | Glyceryl stearate (and) PEG-100 stearate (Arlacel 165 FL ® sold by Uniqema) | 2.00 g |
| | Dimyristyl tartrate (and) cetearyl alcohol (and) C12-15 pareth-7 (and) PPG-25 laureth-25 (Cosmacol PSE ® sold by Sasol) | 1.50 g |
| | Cyclohexasiloxane | 10.00 g |
| | Stearyl alcohol | 1.00 g |
| B | Water | 80.80 g |
| | Phenoxyethanol | 1.00 g |
| | Polyammonium acryldimethyltauramide sold by Clariant under the name Hostacerin AMPS ® | 0.40 g |
| | Xanthan gum | 0.20 g |
| C | Mica/titanium oxide/tin oxide nacre (Timiron Silk Blue ® sold by the company Merck) | 3.00 g |

Example 2

Cosmetic Composition According to the Invention

| | | |
|---|---|---|
| A | Glyceryl stearate (and) PEG-100 stearate (Arlacel 165 FL ® sold by Uniqema) | 2.00 g |
| | Dimyristyl tartrate (and) cetearyl alcohol (and) C12-15 pareth-7 (and) PPG-25 laureth-25 (Cosmacol PSE ® sold by Sasol) | 1.50 g |
| | Cyclohexasiloxane | 10.00 g |
| | Stearyl alcohol | 1.00 g |
| B | Water | 75.75 g |
| | Phenoxyethanol | 1.00 g |
| | Pentasodiumethylenediaminetetramethylenephosphate | 0.05 g |
| | Polyammonium acryldimethyltauramide sold by Clariant under the name Hostacerin AMPS ® | 0.40 g |
| | Xanthan gum | 0.20 g |

-continued

| | |
|---|---|
| C Mica/titanium oxide/tin oxide nacres (Timiron Silk Blue ® sold by the company Merck) | 3.00 g |
| Hollow hemispherical Silicone particles (NLK 510 sold by the company Takemoto Oil and Fats) | 5.00 g |

The lightness and saturation colorimetric values measured according to the protocol described previously, using a MINOLTA CR400® colorimetric chromameter for the composition of Example 2 according to the invention, are the following:

$L=86.46+/-0.04$, $C^*=1.71+/-0.01$.

Figure 2:
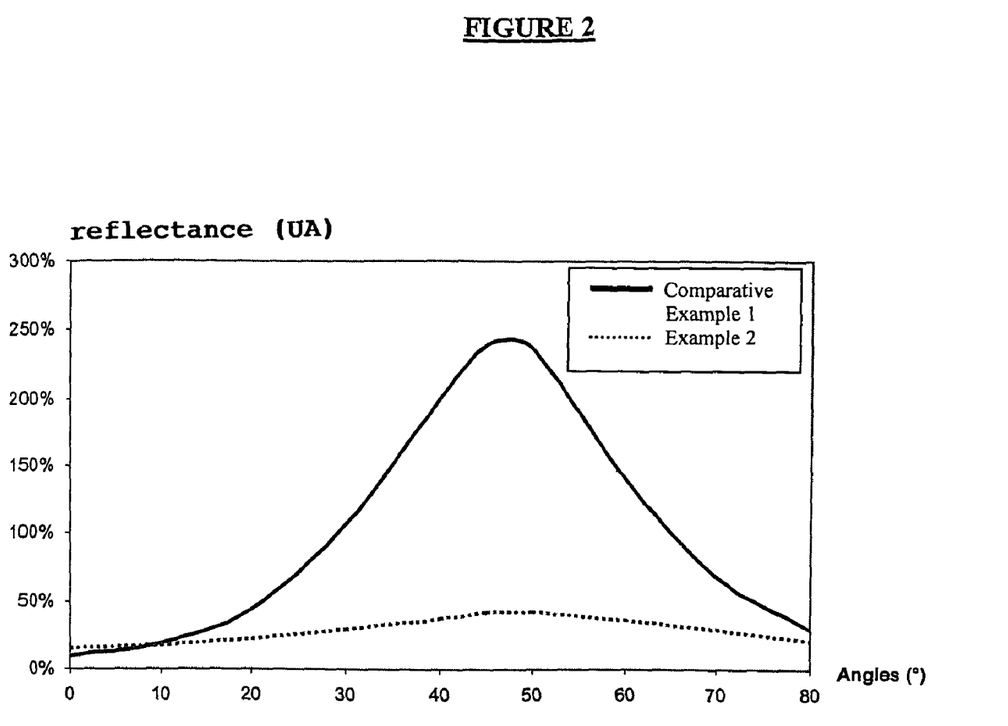
FIG. 2 is a graph showing a relationship between reflectance and observation angle for exemplary cosmetic compositions.

The beneficial effect of the filler/interference particle combination was checked, in comparison with the control composition of Example 1, by measuring the variation in reflectance at the wavelength corresponding to the region of the spectrum in which the reflectance of the Timiron Silk Blue® nacre is the greatest, i.e. at 425 nm, according to the method described previously.

The results are presented in graph form in FIG. 2. It is noted that the control composition has a strong saturation in the specular direction (40-50°), whereas the composition according to the invention has a much more monotonous angular distribution of the reflectance at 425 nm while at the same time remaining non-zero, irrespective of the angle of observation.

The combination in accordance with the invention thus allows homogenization of the color at all angles.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A cosmetic composition for making up and/or caring for skin and/or lips, comprising:
    interference particles having a volume-average size of less than about 40 μm, wherein the interference particles comprise at least one nacre selected from a group consisting of mica/tin oxide/titanium oxide-type nacres and mica/iron oxide/titanium oxide-type nacres; and
    at least one filler having matting power selected from the group consisting of porous silica microparticles, hollow hemispherical silicone particles, and mixtures thereof;
    wherein:
    said filler is such that it gives said composition a matting power of less than 0.8;
    the interference particles and the at least one filler are provided in a physiologically acceptable medium;
    the composition has a lightness L* of greater than about 60 and a saturation C* of less than about 10; and
    a ratio of a weight of the at least one filler to a weight of the interference particles is greater than or equal to 0.8.

2. The composition according to claim 1, wherein the composition has a saturation C* of less than about 5.

3. The composition according to claim 1, wherein the composition has a lightness L* of greater than about 75.

4. The composition according to claim 1, wherein the interference particles have a volume-average size of less than about 30 μm.

5. The composition according to claim 1, wherein the interference particles are present in an amount of less than about 15% by weight relative to a total weight of the composition.

6. The composition according to claim 1, wherein the at least one filler has a volume-average particle size substantially equivalent to the volume-average particle size of the interference particles.

7. The composition according to claim 1, wherein the at least one filler has a refractive index of about 2.2 or less.

8. The composition according to claim 1, further comprising at least one additional filler selected from the group consisting of talc, mica, kaolin, colloidal silica, poly-β-alanine, polyethylene, lauroyllysine, starch, boron nitride, precipitated calcium carbonate, magnesium carbonate, magnesium hydrogen carbonate, barium sulfate, hydroxyapatite, glass or ceramic microcapsules, metal soaps derived from organic carboxylic acids containing from 8 to 22 carbon atoms, and mixtures thereof.

9. The composition according to claim 1, wherein the composition comprises at least one aqueous phase.

10. The composition according to claim 1, wherein the composition comprises at least one fatty phase.

11. The composition according to claim 1, further comprising at least one adjuvant selected from the group consisting of dyes, pigments, optical brighteners, fragrances, preserving agents, physical and chemical sunscreens, sequestrants, pH regulators (acids or bases), and mixtures thereof.

12. The composition according to claim 1, further comprising a film-forming polymer.

13. The composition according to claim 1, wherein the composition is in a form selected from the group consisting of a fluid paste, a serum, a direct, an inverse or multiple emulsion, and an aqueous gel.

14. A method for obtaining a lightening and/or homogenizing effect on skin and/or lips, comprising applying the composition according to claim 1 to the skin and/or lips in an amount sufficient to provide the lightening and/or homogenizing effect.

15. A method for covering skin dyschromia, comprising applying the composition of claim 1 to cover an area of skin having dyschromia.

16. A method for making up skin and/or the lips, comprising applying the composition according to claim 1 to the skin and/or lips.

17. The composition according to claim 1, wherein:
the at least one filler is selected to provide the composition with a variation in reflectance such that a maximum reflectance measured at a top of a reflection peak is less than about 150% and a minimum reflectance measured at a base of the reflection peak is greater than about 5%, the variation in reflectance being measured for observation angles of from 0 to 80° at a wavelength corresponding to a region of the spectrum in which a reflectance of the interference particles is greatest.

18. The composition according to claim 17, wherein the maximum reflectance is less than about 100%.

* * * * *